United States Patent [19]

Arthur

[11] Patent Number: 4,650,767
[45] Date of Patent: Mar. 17, 1987

[54] RESPIROMETER MODULE WITH REPLACEABLE SAMPLE CHAMBER

[75] Inventor: Rober M. Arthur, Fond du Lac, Wis.

[73] Assignee: Tech-Line Instruments, Fond du Lac, Wis.

[21] Appl. No.: 620,819

[22] Filed: Jun. 15, 1984

[51] Int. Cl.⁴ .............................................. C12M 1/16
[52] U.S. Cl. .................................... 435/291; 73/749; 422/68
[58] Field of Search .......................... 435/291; 73/749; 422/68, 79

[56]     References Cited
U.S. PATENT DOCUMENTS 3,314,969  5/1965  Flay .
3,348,409  10/1967  Arthur .
3,740,320  6/1973  Arthur .
4,314,969  2/1982  Arthur et al. .................... 435/291 X
4,462,259  7/1984  Stoltman ............................... 73/749

*Primary Examiner*—Alan Cohan
*Attorney, Agent, or Firm*—Barry E. Sammons

[57]     ABSTRACT

The respirometer module consists of an airtight chamber which includes an air pump, a carbon dioxide scrubber, an electronic gas volume transducer, an air vent, and a fill tube. This single module is combined with separate sample chambers of various sizes and applications. The sample chambers are designed for laboratory, on-line, or submersible application to measure respiration of microorganisms, animals, fish, and plants. The respirometer module which provides air circulation, $CO_2$ absorption, and electronic gas volume sensing can be used interchangeably with any one of these specialized chambers.

5 Claims, 8 Drawing Figures

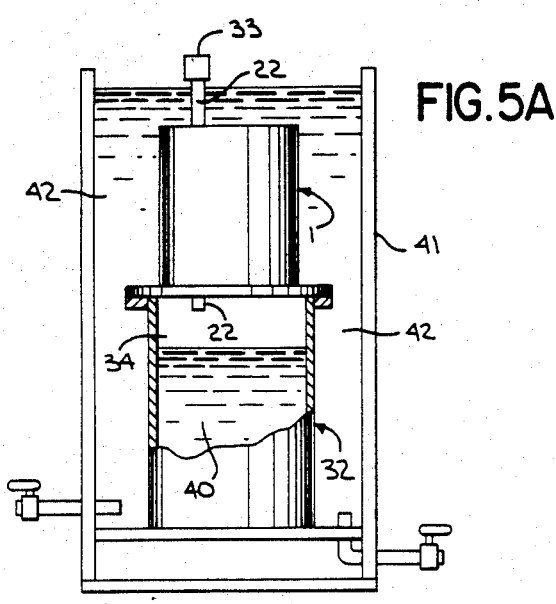
FIG.5A
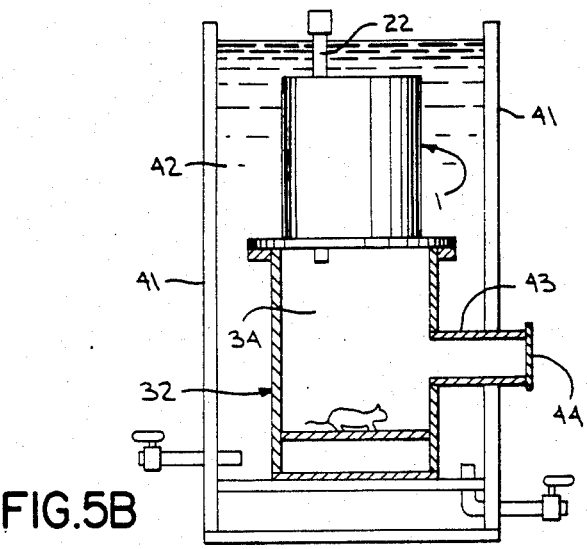
FIG.5B
FIG.5C
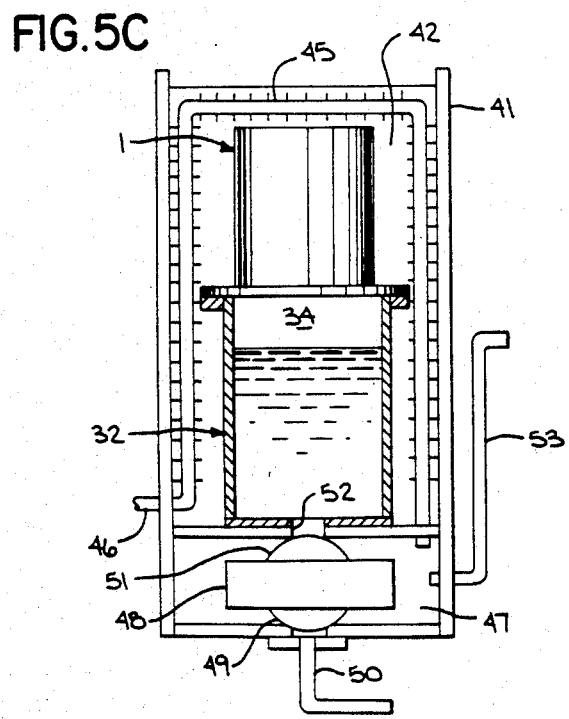
FIG.5D
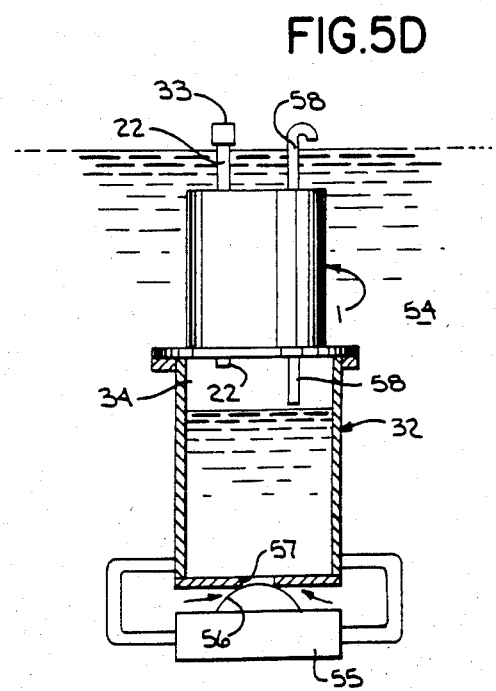

RESPIROMETER MODULE WITH REPLACEABLE SAMPLE CHAMBER

BACKGROUND OF THE INVENTION

Respirometers have been commonly used to determine the metabolic characteristics of cellular suspensions by measuring oxygen requirements during respiration. Measurement of respiration provides the observer with information about the metabolic process which is not available by any other technique. In the biochemical reactions that describe the mechanism of metabolism, utilization of oxygen is intimately related with the energy generation capability of the living system. For this reason measurement of respiration has been used as an indicator of the state of health of a living organism. These measurements are now used in the fields of biomedicine, water pollution, fermentation, and composting on a routine basis as well as in research work.

In the past, respirometers were primarily used in research or diagnostic studies. Small volumes of microorganism cultures were used and the respirometers were manually operated and manually read. Today large volume respirometers, such as those disclosed in U.S. Pat. Nos. 3,348,409; 4,314,969 and 3,740,320, are being used with large samples of cultures obtained from bio-conversion processes such as wastewater treatment, fermentation, and composting. They are also used with small animals and fish. These instruments are automatically operated and are made in laboratory, on-line, and submersible models. The size and varied use of these units has created problems in temperature control, in cleaning, and in maintaining an airtight chamber.

A respirometer in use today for small culture work is known as the Warburg respirometer. The Warburg respirometer consists of a small glass sample flask having a well containing a caustic solution such as KOH. The microorganism culture, suspended in water, is introduced to the flask, KOH is added to the well, and the air space above the suspension is connected to a U-tube manometer. The entire system is mechanically shaken to accelerate oxygen transfer from the air space into the liquid. As microorganisms respire, there is a decrease in the amount of oxygen dissolved in the water and additional gaseous oxygen from the air space is dissolved in the suspension due to mass transfer. Respiration also results in an increase in dissolved carbon dioxide which is transferred from the dissolved state to the gaseous state and is absorbed by the KOH in the well. The net effect is a decrease in the partial pressure of oxygen. The change in pressure is measured by the change in liquid level in a glass U-tube manometer. By utilizing certain calibration procedures, the reading can be interpreted as oxygen utilization in volume or weight units. While the Warburg respirometer is satisfactory for a research environment, it is not appropriate for routine use in connection with bioconversion processes. It is fragile, has a small sample size and is too complicated for automatic operation.

In U.S. Pat. No. 3,348,409 entitled "Method and Apparatus for Analyzing Gas Absorption and Expiration Characteristics," there is described a recording respirometer which measures the rate of oxygen utilized by a respiring culture. This apparatus consists of a large volume sample chamber which contains the culture, a separate carbon dioxide scrubber, an electronic oil manometer (gas volume transducer), and an air pump all connected by tubing. The air pump continuously forces air through the sample chamber to mix and aerate the sample. The air is forced through the scrubber for carbon dioxide absorption, and through the electronic manometer where the change in partial pressure of oxygen is measured. The signal from the electronic manometer is fed to a strip chart recorder to continuously record the oxygen utilization. By using large volume sample chambers and by automating the measurement, this structure did solve certain major disadvantages of the Warburg respirometer. The separation of components and required tubing connections, however, have resulted in problems of maintaining an airtight system and in temperature control. The use of this prior structure with animals, fish, and plants has accentuated the problem of temperature control because to achieve good control it is necessary to place the entire apparatus in a large environmental chamber. Temperature control using such a chamber is not as efficient as using a temperature; controlled water bath.

SUMMARY OF INVENTION

The present invention relates to a universal respirometer module which includes an air pump, a carbon dioxide scrubber, a gas volume transducer, an air vent, and a fill tube all enclosed in a single module which can be connected to numerous separate sample chambers of various size and shape for the purpose of measuring respiration of microorganisms, fish, small animals, and plants. The module coupled with the selected sample chamber is airtight and is completely submerged in a water jacket for temperature control.

A general object of the invention is to provide a single universal module which can interchangeably be connected to many different sized and shaped sample chambers for the purpose of measuring respiration of a wide variety of organisms such as fish, microorganisms, small animals, and plants. The universal module provides in a single unit all the functions common to respirometric measurements including air circulation, carbon dioxide absorption, and sensing of changes in oxygen volume. Coupling this module with sample chambers specially designed to accommodate different forms of living organisms provides for multiple use of a universal module in either a research or production environment.

Another object of the invention is to provide means of air circulation, means of sensing the volume of oxygen utilized, and means of scrubbing out carbon dioxide all in a single universal module. The inclusion of all of these components in a single airtight chamber eliminates the need to provide airtight tubing connections between the various components and, therefore, eliminates the problem of tubing leaks common with prior respirometers.

A third objective of the invention is to provide a universal respirometer module which can be used in a variety of applications as a laboratory instrument, as an on-line process control instrument, or as a submersible instrument. In a laboratory application the module is coupled with a selected sample chamber and may be completely submerged in a water jacket. The water jacket assures temperature stability and provides the means to test respiration at any temperature by control of the water bath temperature. In an on-line application the module is connected to a selected submersible sample chamber and can be completely submerged in a water jacket. Liquid samples are automatically and sequentially introduced into the sample chamber to determine the respiration characteristic of a wastewater treatment process or fermentation system. The temperature of the test can be controlled by controlling the temperature of the water jacket. On the other hand, the universal module can also be connected to a selected sample chamber and completely submerged in a treatment process tank or a stream or lake to measure the in situ respiration activity of microorganisms, plants, and fish under natural tempearture conditions.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 5A is a pictoral view of the respirometer module connected to a sample chamber designed for analyzing mass cultures of microorganisms suspended in a liquid. The module and the sample chamber are both submerged in a water jacket for temperature control.

FIG. 5B is a pictoral view of the respirometer module connected to a sample chamber having a side port entry for use with small animals. Again, both module and sample chamber are submerged in a water jacket.

FIG. 5C is a pictoral view of the respirometer module used with a sample chamber which is designed for on-line use. The sample continuously flows through a heat exchanger in the water-jacketed tank surrounding the module and sample chamber.

FIG. 5D is a pictoral view of the respirometer module connected to a special chamber which is used to sample in situ the respiration of microorganisms in a process tank.

DESCRIPTION OF THE PREFERRED EMBODIMENT

Figure 1:
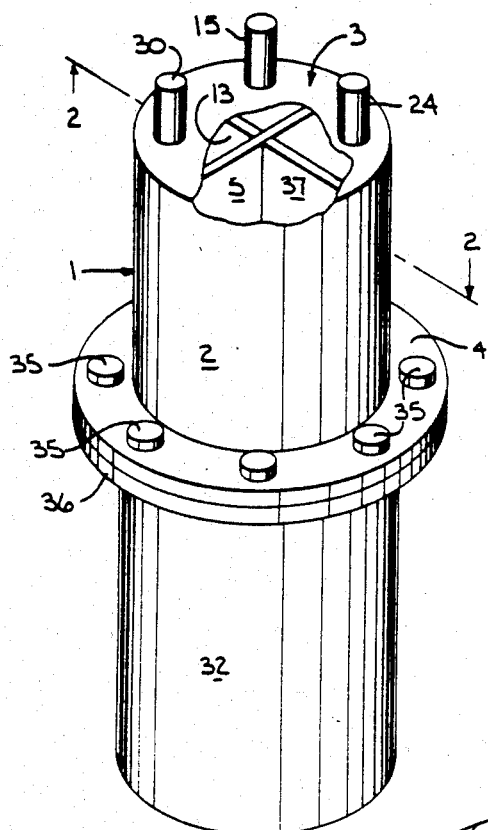
FIG. 1 is a perspective view with part cut away of the invented respirometer module and a selected sample chamber.
Figure 2:
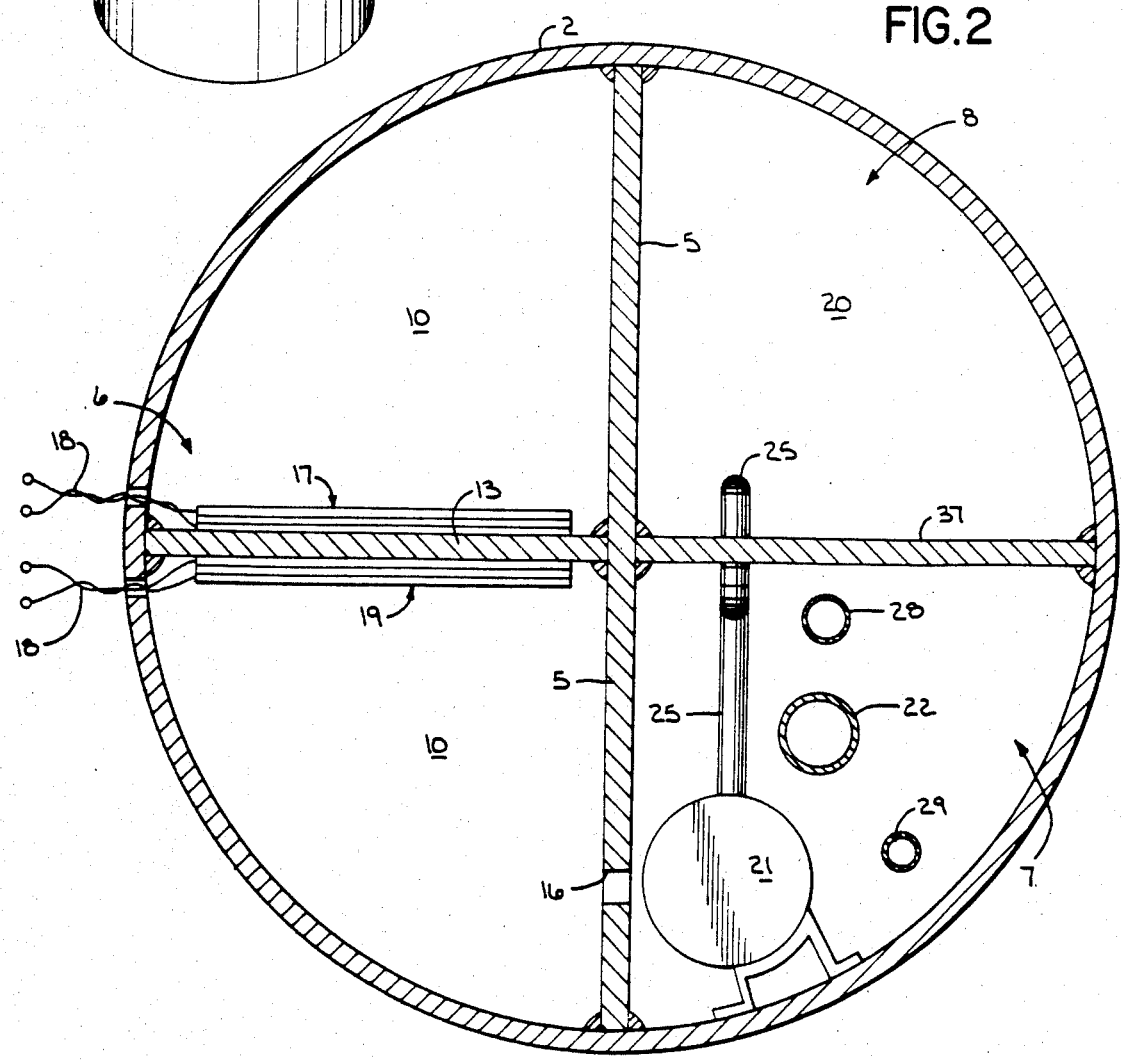
FIG. 2 is a view in cross section taken along the plan 2—2 of the respirometer module in FIG. 1.

Referring particularly to FIGS. 1 and 2, the respirometer module 1 includes an enclosure formed by a circular cylindrical side wall 2, an airtight top 3, and a bottom 4. The respirometer module 1 is mechanically connected to a sample chamber 32 by a set of bolts 35 which extend through a flange formed by the bottom 4 and a lip 36 formed around the circular top of the sample chamber 32. The respirometer module 1 includes a divider wall 5 which extends through its center from the top 3 to the bottom 4, and which defines a compartment 6 that occupies one half the interior of the module 1. The other half of the interior is further divided by a partition 37 to form a pair of compartments 7 and 8.

Figure 3:
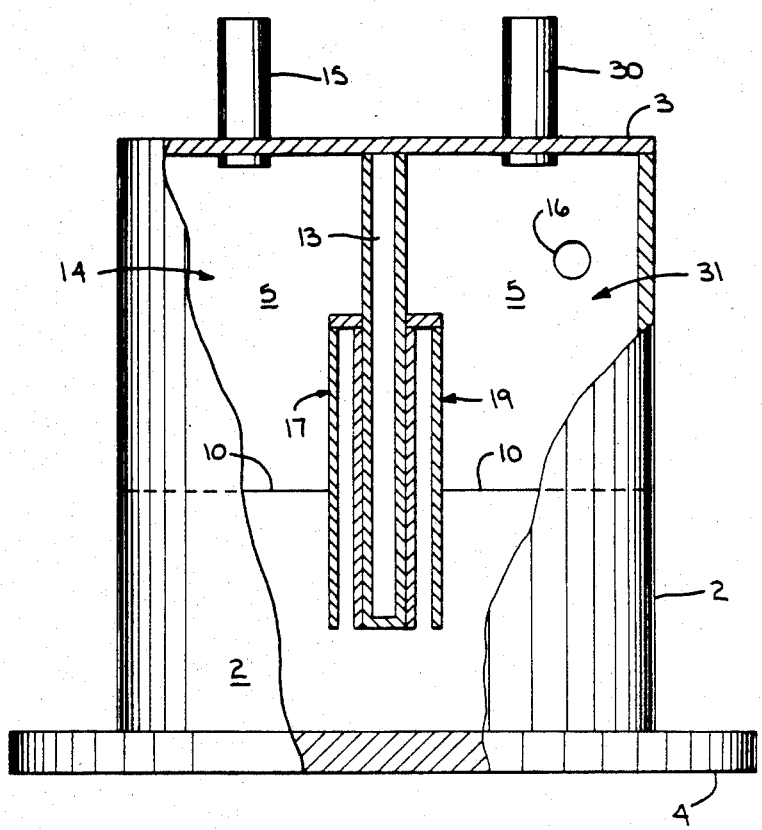
FIG. 3 is an elevation view with parts cut away showing the gas volume transducer which forms part of the respirometer module of FIG. 1.

The compartment 6 houses a gas volume transducer. As shown best in FIGS. 2 and 3, the lower portion of the compartment 6 contains a manometer oil 10 and a barrier 13 extends downward from the top 3 into this oil 10. An air space 14 is thus formed above the oil 10 to one side of the barrier 13, and an air space 31 is formed on the other side. Air space 14 is vented to atmospheric pressure by a tube 15 which passes through the top 3, and the air space 31 is vented to the compartment 7 by an opening 16 in the divider wall 5. A feed line 30 extends into the compartment 6 through the top 3, and a measured amount of manometer oil may be introduced by operating a normally closed valve (not shown in the drawings).

The difference in oil level on each side of the barrier 13 is a measure of the air pressure in the air space 31 with respect to atmospheric pressure. This difference is measured electrically by a pair of capacitors 17 and 19 which are formed on the sides of the barrier 13. The manometer oil 10 flows between the plates of each capacitor 17 and 19, and the high dielectric constant of the oil alters their capacitance. The relative levels of the oil 10 in the respective spaces 14 and 31 is thus sensed by measuring the relative capacitance of the capacitors 17 and 19. This is accomplished by connecting the capacitors 17 and 19 to a bridge circuit (not shown in the drawings) through wires 18. The bridge circuit produces an electrical signal which is directly proportional to the air pressure in the space 31 relative to atmospheric pressure.

Figure 4:
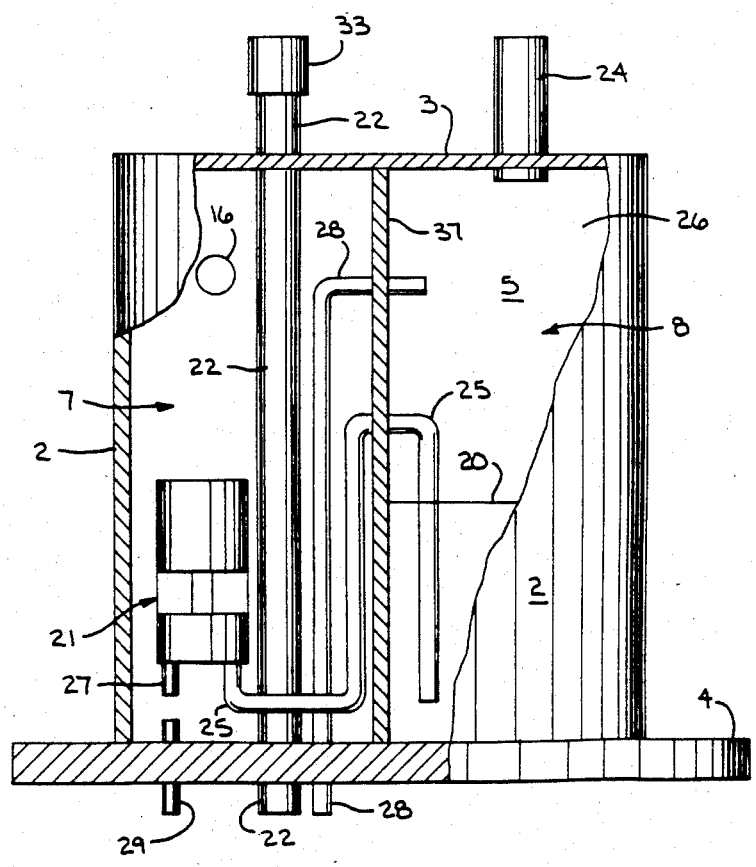
FIG. 4 is an elevation view with parts cut away showing the pump compartment and carbon dioxide remover compartment which form parts of the respirometer module of FIG. 1.

Referring particularly to FIGS. 2 and 4, the compartment 8 in the respirometer module 1 contains a solution of potassium hydroxide 20 which is added to measured amounts through a feed line 24 in the top 3. Air is introduced into the solution 20 through air tube 25 which passes through the partition 37 and extends downward into the solution 20. Air is removed from the space 26 above the solution 20 by a second air tube 28 which exits through the partition 37 and extends downward through the bottom 4 in the compartment 7.

The compartment 8 functions to remove carbon dioxide from the air which is circulated through the potassium hydroxide solution 20. As will now be described, the air is drawn from the sample chamber 32, "scrubbed" by the solution 20 to remove carbon dioxide, and recirculated back to the sample chamber 32.

Referring particularly to FIGS. 2 and 4, the compartment 7 formed in the respirometer module 1 houses an air pump 21 and provides space for a number of conduits and air tubes. The air pump 21 has an air intake 27 from the space defined by compartment 7, and an outlet which connects to air tube 25. The compartment 7 is coupled to the gas volume transducer through opening 16, and it is coupled to the sample chamber 32 by a tube 29 which extends through the bottom 4. A sample inlet pipe 22 extends downward through the compartment 7 and it is closed at the top by a cap 33. The air tubes 25 and 28 also pass through the compartment 7.

In operation, 500 ml of manometer oil 10 and 200 ml of potassium hydroxide solution 20 are introduced into the respective compartments 6 and 8. The respirometer module 1 is then fastened to a suitable sample chamber 32 and the air pump 21 is started. Air from the sample chamber 32 is fed through the solution 20 to remove carbon dioxide produced by respiring organisms in the sample chamber 32. The net effect of this process is a reduction in the partial pressure of oxygen as it is consumed by the organisms. This reduction in oxygen is transferred as a reduction in air pressure through the compartment 7 to the air space 31 in the gas volume transducer. The oil 10 thus rises to increase the capacitance of capacitor 19 and drops on the other side of the barrier 13 to decrease the capacitance of capacitor 17. This difference is proportional to the amount of oxygen consumed by the organisms in the sample chamber 32.

Referring particularly to FIGS. 5A–5D, the respirometer module of the present invention may be used with a variety of sample chambers and in a variety of environments. In FIG. 5A for example, the respirometer module 1 connects to a sample chamber 32 designed for analyzing mass cultures of microorganisms suspended in a liquid 40. The module 1 and attached sample chamber 32 are both submerged in a tank 41 which provides a water jacket 42 having a controlled temperature. The microorganisms remove oxygen from the air space 34 as they respire and the amount is measured by the respirometer module 1. The microorganisms may be introduced into the chamber 32 by removing the cap 33 and pouring, or pumping them through the sample inlet pipe 22.

A different sample chamber 32 is employed when the respiration rate of small animals is measured as shown in FIG. 5B. In this instance the small animal is introduced into the chamber 32 through a passage 43 having an airtight door 44. The oxygen removed from the air space 34 is measured by the respirometer module 1.

The arrangement shown in FIG. 5C is employed when the respirometer is placed "on-line" to measure the respiration of microorganisms suspended in a liquid. The respirometer module 1 and sample chamber 32 are both submerged in a tank 41 filled with water 42. The sample material is pumped into a heat exchanger 45 at inlet 46, and it flows into a chamber 47 formed beneath the tank 41. A diaphragm valve 48 is mounted inside the chamber 47 and it includes a lower diaphragm 49 which covers an opening to a drain 50, and an upper diaphragm 51 which covers an opening 52 into the bottom of the sample chamber 32. When the upper diaphragm 51 is open, sample fluid flows into the chamber 32 until the level rises to a point at which the fluid overflows through pipe 53. The upper diaphragm valve 51 is then closed, the lower diaphragm valve 49 is opened, and fluid is pumped through the heat exchanger 45, through the lower chamber 47 and out the drain 50 while the respirometer 1 makes its measurement on the sample entrapped in the chamber 32. This continuous flow of fluid maintains the water jacket 42 at the ambient temperature of the body of liquid from which the sample was pumped.

The fourth embodiment of the invention shown in FIG. 5D is a submersible respirometer. In this structure the respirometer module 1 and attached sample chamber 32 are submerged in the body of liquid 54 to be sampled. A diaphragm valve 55 is fastened to the bottom of the sample chamber 32 and its diaphragm 56 covers an opening 57 in the bottom of the chamber 32. When the diaphragm valve 55 is opened, sample fluid flows into the chamber until the level reaches the bottom end of a vent 58. Respiration is then measured as described above at the precise temperature of the body of liquid 54 from which the sample was taken. When the measurement is complete, the diaphragm valve 55 is opened and compressed air is applied through the inlet pipe 22 to force the sample from the chamber 32. The measurement cycle is then repeated.

It should be apparent to those skilled in the art that the respirometer module of the present invention is easily used with a variety of sample chambers and in a variety of applications.

What is claimed is:

1. A respirometer module for use with any one of a plurality of sample chambers, the combination comprising:

an enclosure having a bottom which is releasably fastened to one of said sample chambers containing a sample material that consumes oxygen in the air space within the sample chamber;

a carbon dioxide scrubber which includes a liquid disposed in a first compartment formed inside the enclosure;

an air pump for circulating air from the air space in the sample chamber through the liquid in the carbon dioxide scrubber, the air pump being mounted inside the enclosure and including the air intake which couples to the sample chamber through an opening in the bottom of the enclosure; and a gas volume transducer formed within a second compartment in the enclosure and including an inlet which is coupled to the air space in the sample chamber and a vent which is coupled to atmospheric pressure, the gas volume transducer being operable to generate an electrical signal which indicates the difference in the air pressure in the sample chamber from atmospheric pressure.

2. The respirometer module as recited in claim 1 in which the gas volume transducer includes a pair of capacitors mounted to opposite sides of a barrier which extends downward into a manometer oil, and the inlet communicates with the air space above the manometer oil to one side of the barrier and the vent communicates with the air space above the manometer oil to the other side of the barrier.

3. The respirometer module as recited in claim 1 in which the fluid employed in the carbon dioxide scrubber is potassium hydroxide.

4. The respirometer module as recited in claim 1 in which the interior of the enclosure is divided into three compartments, with the carbon dioxide scrubber occupying one compartment, the gas volume transducer occupying a second compartment and the air pump being disposed in the third compartment.

5. The respirometer module as recited in claim 4 in which an inlet pipe extends through the enclosure from top to bottom and communicates with the interior of the sample chamber.

* * * * *